(12) United States Patent
Kiran et al.

(10) Patent No.: US 9,493,792 B1
(45) Date of Patent: Nov. 15, 2016

(54) PROCESS FOR PRODUCTION OF YELLOW PIGMENT FROM BACTERIA

(71) Applicant: KING SAUD UNIVERSITY, Riyadh (SA)

(72) Inventors: George Seghal Kiran, Puducherry (IN); Naif Abdullah Al-Dhabi, Riyadh (SA); Mariadhas Valan Arasu, Riyadh (SA); Joseph Selvin, Puducherry (IN)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/971,468

(22) Filed: Dec. 16, 2015

(51) Int. Cl.
*C12P 7/26* (2006.01)
*C12P 23/00* (2006.01)
*C12N 1/20* (2006.01)
*C12P 5/02* (2006.01)
*C12P 39/00* (2006.01)
*C12N 9/52* (2006.01)

(52) U.S. Cl.
CPC .................. *C12P 5/026* (2013.01); *C12N 9/52* (2013.01); *C12P 23/00* (2013.01); *C12P 39/00* (2013.01)

(58) Field of Classification Search
CPC ............ C12P 39/00; C12N 1/20; C12N 9/52
USPC .............................................. 435/67, 252.31
See application file for complete search history.

(56) References Cited

FOREIGN PATENT DOCUMENTS

CN     102899265 A     1/2013

OTHER PUBLICATIONS

Khaneja et al. J. Appld Microbiol, 2010, 108, pp. 1889-1902.*
Perez-Fons et al. Biochim. Biophy acta 2011, 1811, pp. 177-185.*
English translation of CN102899265, published Jan. 30, 2013.*

* cited by examiner

*Primary Examiner* — Robert Mondesi
*Assistant Examiner* — Md. Younus Meah
(74) *Attorney, Agent, or Firm* — Richard C. Litman

(57) ABSTRACT

The process for the production of the yellow pigment can include the steps of (a) culturing *Bacillus* sp. GSK07 bacteria; and (b) extracting the yellow pigment from the bacterial culture using a solvent. The solvent for extraction can be an alcohol, e.g., ethanol, methanol, or both ethanol and methanol. The pigment includes D-limonene.

4 Claims, 4 Drawing Sheets

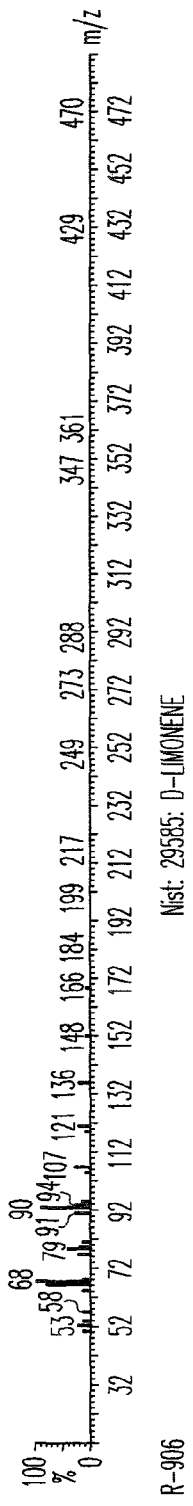
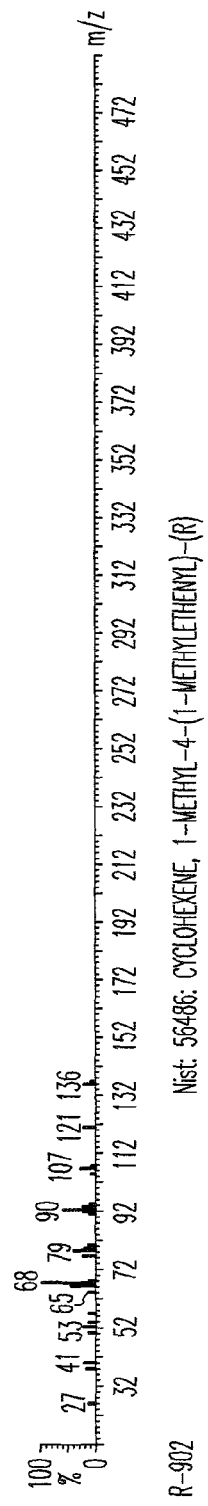
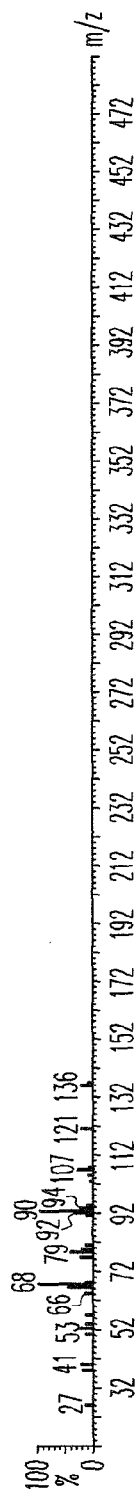

PROCESS FOR PRODUCTION OF YELLOW PIGMENT FROM BACTERIA

BACKGROUND OF THE INVENTION

1. Field of the Invention

The present invention relates to natural pigments and flavoring agents, and particularly to a method for producing a yellow pigment using bacteria.

2. Description of the Related Art

Flavor is the combination of taste and odor and it is usually the result of the presence, within complex matrices, of many volatile and nonvolatile components possessing diverse chemical and physicochemical properties. Whereas the nonvolatile compounds contribute mainly to the taste, the volatile ones influence both taste and aroma. A vast array of compounds maybe responsible for the aroma of the food products.

Many flavoring compounds are conventionally produced by chemical synthesis. A growing aversion of the consumer towards chemicals added to food, cosmetics and other household products has induced companies to direct their attention towards flavor compounds of biological origin, so called natural or bio-flavors. Thus, it would be desirable to produce a food coloring and/or pigment from natural sources.

Thus, a method of synthesizing a pigment that is also useful for providing flavoring and fragrance solving the aforementioned problems is desired.

SUMMARY OF THE INVENTION

A process for producing yellow pigment from bacteria includes the steps of (a) culturing a bacterial species of the genus *Bacillus*; and (b) extracting the yellow pigment from the bacterial culture using a solvent. The pigment is terpene based. The bacteria can be *Bacillus* sp. GSK07. Preferably, the bacterial culture is incubated in a nutrient broth at about 30° C. for about 5-7 days. The solvent for extraction can be an alcohol, e.g., ethanol, methanol, or both ethanol and methanol. The pigment includes D-limonene.

These and other features of the present invention will become readily apparent upon further review of the following specification and drawings.

BRIEF DESCRIPTION OF THE DRAWINGS

FIG. 1A shows the mass spectrum of D-liomonene. FIG. 1B shows the mass spectrum of cyclohexene 1-methyl-4-(1-methylethenyl). FIG. 1C shows the mass spectrum of cyclohexene 1-methyl-5-(1-methylethenyl).

Similar reference characters denote corresponding features consistently throughout the attached drawings.

DETAILED DESCRIPTION OF THE PREFERRED EMBODIMENTS

Figure 2:
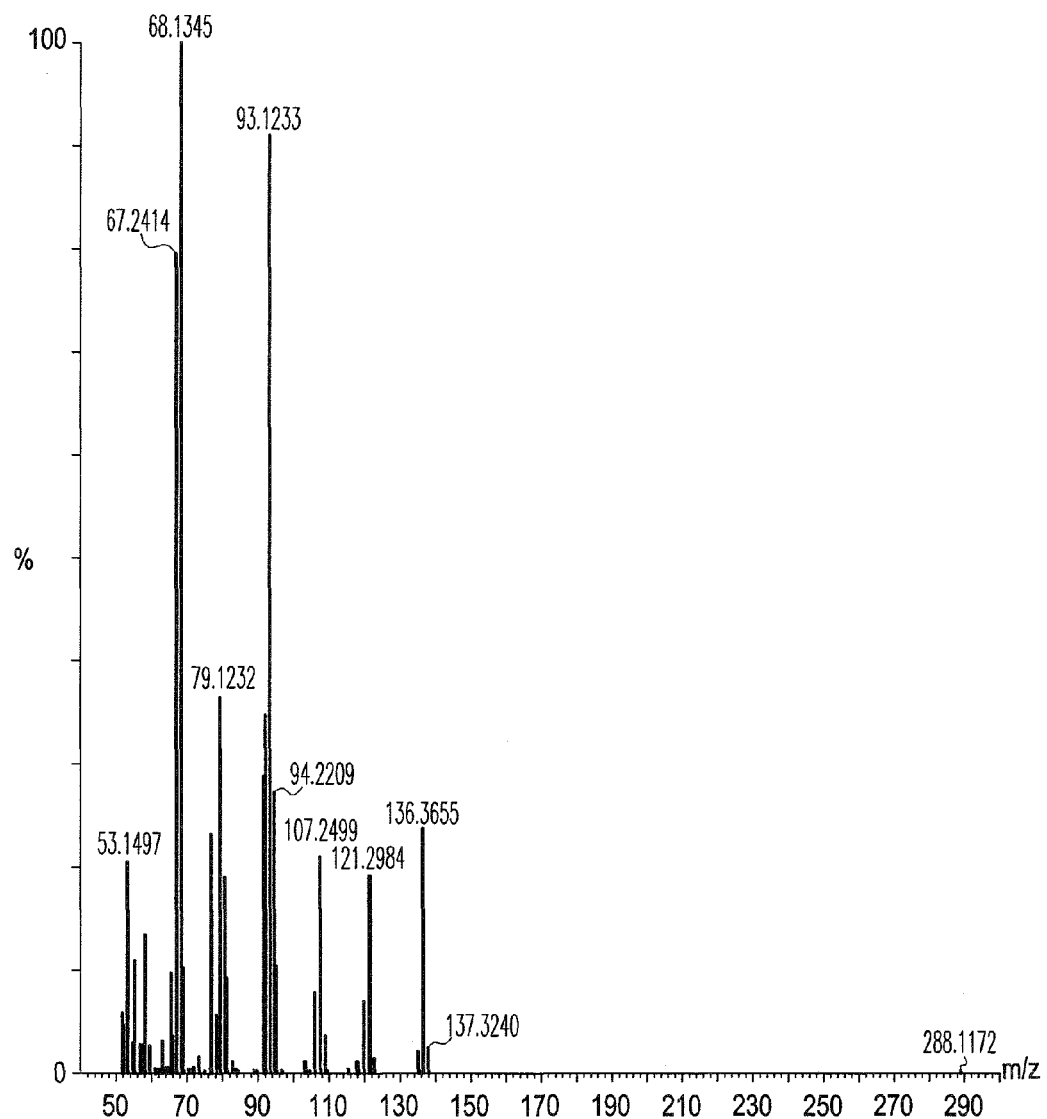
FIG. 2 shows a graph of the mass spectrum of the yellow bacterial pigment from *Bacillus* sp. GSK07 having an m/z of 136.

A process for producing yellow pigment from bacteria can include the steps of (a) culturing a bacterial species of the genus *Bacillus*; and (b) extracting the yellow pigment from the bacterial culture using a solvent. The bacteria can be *Bacillus* sp. GSK07. Preferably, the bacterial culture is incubated in a nutrient broth at about 30° C. for about 5-7 days. One or more solvents can be used for extraction of the pigment from the culture. The solvent for extraction is preferably an alcohol, e.g., ethanol, methanol, or both ethanol and methanol.

The pigment includes D-limonene, a volatile flavor compound. FIG. 1A shows a graph of a mass spectrum of D-Limonene. FIG. 1B is the mass spectrum of cyclohexene 1-methyl-4-(1-methylethenyl) at FIG. 1C is the mass spectrum of cyclohexene 1-methyl-5-(1-methylethenyl). Limonene is typically used as an additive in food and as fragrance.

A novel species of bacteria, identified as *Bacillus* sp. GSK07, was isolated by the present inventors from soil samples near brackish waters. It was found that the bacteria are capable of producing and secreting a yellow pigment. The yellow pigment was obtained by fermentation under submerged culture. By optimizing the nutrient medium with carbon, nitrogen, and inorganic substances, the yield was substantially increased to 5.2 g/L. The bacteria was determined by 16S ribosomal RNA gene homology to be a species of *Bacillus*. It was found that *Bacillus* sp. GSK07 secretes at least one pigment during its life cycle. The pigment has a yellow color and a limonene flavor. It was determined that the pigment includes limonene.

The yellow pigment obtained from *Bacillus* sp. GSK07 could be useful for providing coloring, flavoring, and/or fragrance for food, cosmetic, chemical and pharmaceutical products. The pigment can also provide good antioxidant activity.

The pigment produced by the present methods can also be used for food packaging. Recent studies have proven the feasibility of using D-limonene as a natural PLA plasticizer to obtain flexible films for food contact materials and even to be tested as active compounds in active packaging systems. For example, recent studies have been conducted on the use of limonene as a new novel monomer to obtain poly-terpenes. The limonene diffusion through packaging has also been widely studied in different food contact materials such as polyethylene, low density polyethylene (LDPE), high density polyethylene (HDPE), polystyrene (PS) and PLA. It was found that the addition of limonene into the PLA (poly-lactic acid) matrix decreases the glass transition temperature of the films. The cold crystallization temperature and degree of crystallinity decreased while $T_m$ was slightly reduced. Mechanical properties of the films altered by the presence of limonene and good plasticization were observed. Barrier properties to oxygen reduced due to the plasticization of the PLA matrix, but presented acceptable values for food packaging applications. Furthermore, D-limonene reduced the water adsorption of PLA matrix. These results show the feasibility of using D-limonene as a natural PLA plasticizer.

The following examples will further illustrate the process for producing yellow pigment from bacteria.

Example 1

Extraction of a Yellow Pigment from *Bacillus* sp. GSK07

A *Bacillus* sp. GSK07 was isolated from soil samples near brackish waters of Pondicherry, India. The isolated bacteria was cultured on nutrient agar plates. Based on color, the isolated strain was identified as a yellow pigment producer.

Colony morphology, biochemical characteristics, and 16S rRNA analysis (forward and reverse sequence) showed it belongs to *Bacillus* sp. GSK07. The bacterium was cultured in nutrient broth with 5-7 days and incubated at 30° C. to yield maximum yellow pigment. By optimizing the nutrient medium with carbon, nitrogen, and inorganic substances, the yield was substantially increased to 5.2 g/L. Suitable extraction solvents were optimized to extract all of the pigment from the cells. The extraction was continued until the cells became colorless. Ethanol followed by methanol extraction was found to successfully extract all of the pigment from the cells. The solvent was evaporated in a rotary evaporator and the stability of the pigment in response to changes in light, pH, temperature and salt was studied. The pigment was stable up to 80° C., at pH 2.0 to pH 8.0, and 4% NaCl concentration. FIG. 2 shows a graph of the mass spectrum of the yellow bacterial pigment from *Bacillus* sp. GSK07 having an m/z of 136, indicating that the compound is limonene. A comparison of the spectrum in FIG. 2 and the NIST library spectra of FIGS. 1A-1C confirms that the compound can be identified as limonene.

Example 2

Effect of the Color of Light on the Yield of the Yellow Pigment

Figure 3:
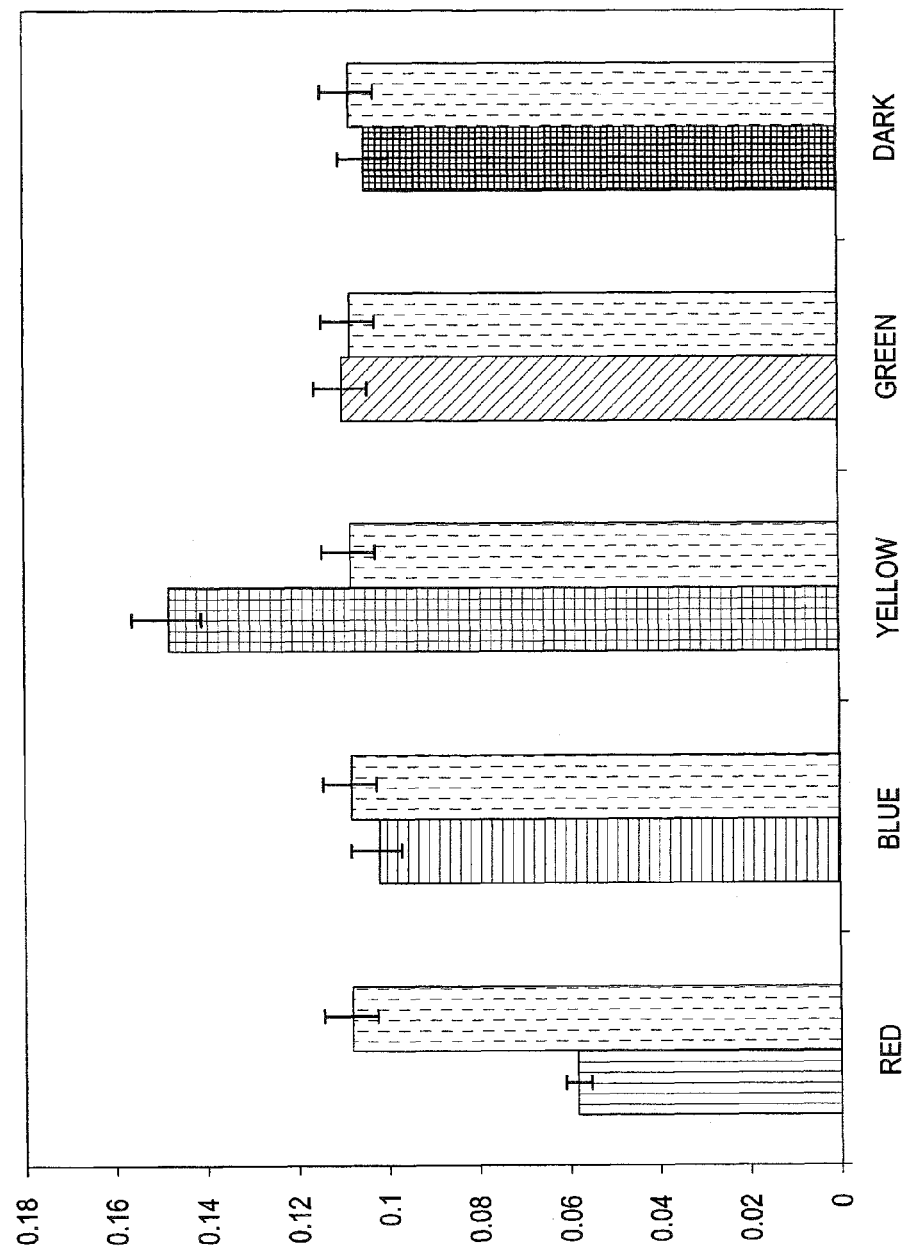
FIG. 3 shows the intensity of the yellow pigment based on the color of the light versus control.
Figure 4:
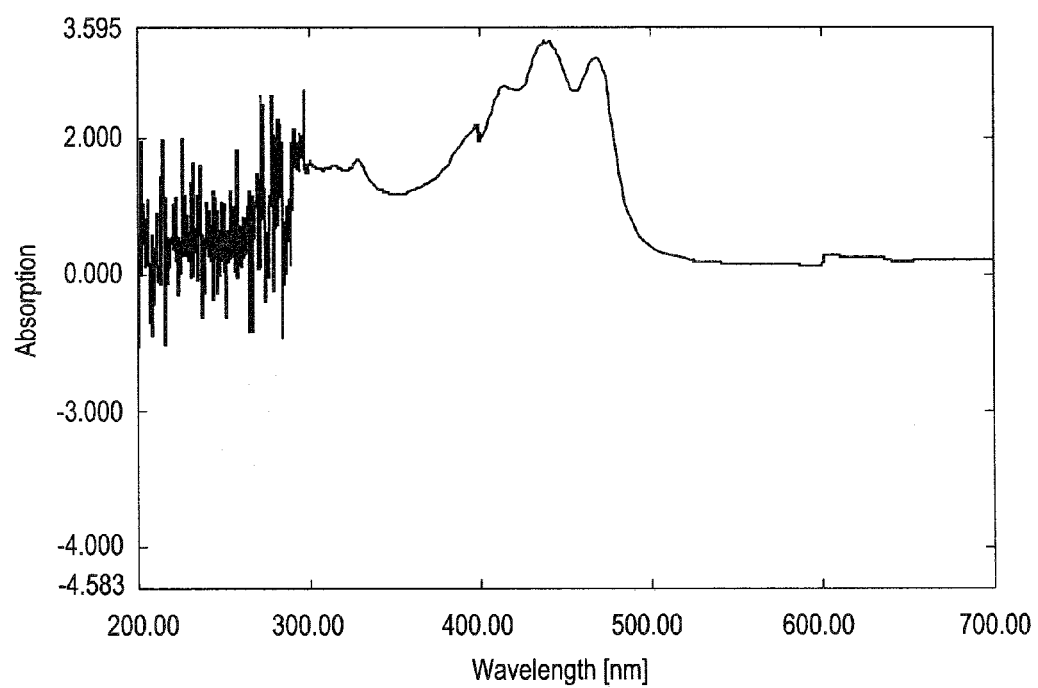
FIG. 4 is a UV-Vis spectrum of the yellow pigment from *Bacillus* sp. GSK07 which shows maximum absorbance at 450 nm.

The isolated *Bacillus* sp. GSK07 bacteria was cultured on nutrient agar plates. The bacterium was cultured in nutrient broth with 5-7 days and incubation at 30° C. to increase the production of the yellow pigment. The culture was subjected to various lights. The intensity of pigment was determined by UV-Vis spectrophotometer at 420-450 nm and by color flux. FIG. 3 shows the intensity of the yellow pigment based on the color of the light versus control. The biomass and pigment yield was better in yellow light, compared to dark lights. For example, using 1-2% yellow light increased yield of the pigment, but red light reduced the intensity of pigment. FIG. 4 is a UV-Vis spectrum of the yellow pigment from *Bacillus* sp. GSK07 which shows maximum absorbance at 450 nm.

The results show that light has great influence on pigment production. When the bacteria are exposed to various lights, it was found that the biomass and the pigment yield was better in yellow light, compared to the dark lights. Utilization of light is an important concept in ecological theory, which is clearly reviewed by other researchers. Light plays an important role in niche differentiation, which reduces competition between species and promotes living together. The experiment shows that the *Bacillus* GSK07 absorbs yellow light more than the other spectrum of lights for its growth and pigment production.

The total phenolic content was determined. The terpenoid assay and antioxidant assay was carried out by DPPH. The GC-MS analysis of the pigment indicated that the pigment has volatile flavor compounds D-limonene in the retention time of 5.875.

It is to be understood that the present invention is not limited to the embodiments described above, but encompasses any and all embodiments within the scope of the following claims.

We claim:
1. A process for production of yellow pigment from bacteria, comprising the steps of:
   (a) culturing a bacterial species of the genus *Bacillus* to provide a bacterial culture; and
   (b) extracting a yellow pigment from the bacterial culture using a solvent, wherein the pigment comprises D-limonene.
2. The process for production of yellow pigment from bacteria according to claim 1, wherein said culturing occurs at about 30° C. for at least 5 days.
3. The process for production of yellow pigment from bacteria according to claim 1, wherein the bacterial species of the genus *Bacillus* secretes the yellow pigment at least once during its life cycle.
4. The process for production of yellow pigment from bacteria according to claim 1, wherein the solvent comprises at least one of ethanol and methanol.

* * * * *